United States Patent [19]

Croce, Jr.

[11] Patent Number: 4,858,126

[45] Date of Patent: Aug. 15, 1989

[54] METHOD AND APPARATUS FOR QUANTITATIVE EVALUATION OF BACK HEALTH

[76] Inventor: Pasquale W. Croce, Jr., 977 Derring La., Bryn Mawr, Pa. 19010

[21] Appl. No.: 18,994

[22] Filed: Feb. 26, 1987

[51] Int. Cl.⁴ ............................................. G06F 15/32
[52] U.S. Cl. ................................ 364/413.02; 128/774
[58] Field of Search ................ 364/415; 128/781–782; 73/379–381, 865.1

[56] References Cited

U.S. PATENT DOCUMENTS

| | | | |
|---|---|---|---|
| 2,763,935 | 9/1956 | Whaley et al. | 33/169 |
| 3,680,386 | 8/1972 | Cannon | 73/379 |
| 3,752,144 | 8/1973 | Weigle, Jr. | 128/2 |
| 3,991,745 | 11/1976 | Yoslow et al. | 128/2 |
| 4,036,213 | 7/1977 | Gregory | 128/2 |
| 4,108,164 | 4/1978 | Hall, Sr. | 128/781 |
| 4,144,568 | 3/1979 | Hiller et al. | 364/410 |
| 4,306,571 | 11/1981 | McLeod, Jr. | 128/782 |
| 4,375,674 | 1/1983 | Thornton | 364/559 |
| 4,416,293 | 11/1983 | Anderson et al. | 128/782 |
| 4,425,713 | 1/1984 | Rotella | 33/174 |
| 4,436,099 | 3/1984 | Raftopoulos | 128/782 |
| 4,485,825 | 12/1984 | Domjan et al. | 128/774 |
| 4,528,990 | 7/1985 | Knowles | 128/782 |
| 4,592,371 | 6/1986 | Pelicano | 128/774 |
| 4,655,227 | 4/1987 | Gracovetsky | 128/782 |
| 4,664,130 | 5/1987 | Gracovetsky | 128/781 |
| 4,665,928 | 5/1987 | Linial | 128/782 |
| 4,699,156 | 10/1987 | Gracovetsky | 128/781 |
| 4,708,148 | 11/1987 | Olson | 128/781 |

*Primary Examiner*—Jerry Smith
*Assistant Examiner*—Gail O. Hayes
*Attorney, Agent, or Firm*—Woodcock Washburn Kurtz Mackiewicz & Norris

[57] ABSTRACT

Disclosed are methods and apparatus for determining the furnctional capabilities of bodies. More particularly, methods and apparatus for reliably producing a numerical index of the state of health of a patient's back are disclosed. The method generally comprises positioning the patient in a first position, usually on a rigid flat surface. With the patient so positioned, the physician then measures the ability of the patient to perform certain movements with the first portion of the body while the patient attempts to maintain the remainder of the body in a substantially stationary position. Such movements will contain some indicia of the relative health of the patient's back, and the measurements thereof quantify such indicia. Measuring the movements will generally include measuring the angle and/or distance covered or subtended by the first portion of the body, the remaining portion of the body, or both as the patient proceeds through the designated movement. The percent of body fat of the patient being tested is also generally measured. These measurements are then compared to an expected range of measured values to generate an index indicative of the relative health of the patient's back.

26 Claims, 2 Drawing Sheets

METHOD AND APPARATUS FOR QUANTITATIVE EVALUATION OF BACK HEALTH

BACKGROUND OF THE INVENTION

The present invention pertains to methods and apparatus for the determination of functional capability of bodies. More particularly, the present invention relates to apparatus and methods for quantitatively determining the relative injury or health of a human back.

There is perhaps no injury that a human body can sustain which is more frustrating and debilitating than back injury. However, no acceptable medical diagnostic apparatus or method has heretofore been developed which is suitable for properly evaluating the condition and/or rehabilitation progress of a patient suffering from back injury. This inability of the treating physician to quantify the extent of back injury and the recovery therefrom causes uncertainty in the treatment protocol as well as psychological uneasiness in the patient being treated. This inability to quantify back injury has unfortunately also frequently been the source of fraudulent medical claims against insurance carriers and the like. According to heretofore used techniques, the physician or physical therapist would generally ask the patient to perform some arbitrary task, such as exerting some force on the examining physician or therapist, or to perform a certain movement. The physician then endeavors to recall from his past experience whether or not such movement or force is indicative of back pain or injury. The reliability of such an inherently qualitative procedure is questionable and subject to error.

While attempts to provide a quantitative measure of muscular condition have previously been made, such prior devices and methods were not specifically directed or adapted to the diagnosis and testing of back injury. For example, U.S. Pat. No. 3,252,144 to Weigle discloses an apparatus and method which measures the force applied to various sensors. The disadvantage of such methods and apparatus is that muscular strength is the sole source of input to the diagnostic technique. In addition, the methods disclosed in Weigle generally require a relatively complex cumbersome, and expensive testing apparatus.

SUMMARY OF THE INVENTION

The present invention provides a substantial step forward in the diagnosis and treatment of back injury and in the ability of physicians and insurance carriers to identify fraudulent claims of back injury.

It is an object of the present invention to provide methods and apparatus for precisely quantifying the relative health or injury of a patient's back.

It is a further object of the present invention to provide a method and apparatus for easily quantifying the extent of a back injury.

One embodiment of the present invention provides a method for quantitatively establishing the health of the back of a human patient. This method comprises positioning the patient in a first position, usually on a rigid flat surface. With the patient so positioned, the physician measures, with the aid of a goniometer for example, the ability of the patient to perform movements with a first portion of the body while attempting to maintain the remainder of the body in a substantially stationary position. This movement will contain some indicia of the relative health of the patient's back, and the measurement thereof quantifies such indicia. The measuring step generally includes measuring the angle and/or distance covered or subtended by the first portion of the body, the remaining portion of the body, or both as the patient proceeds through the designated movement. These measurements are then compared to an expected range of measured values to generate an index indicative of the relative health of the patient's back.

DETAILED DESCRIPTION OF PREFERRED EMBODIMENTS

Figure 2:
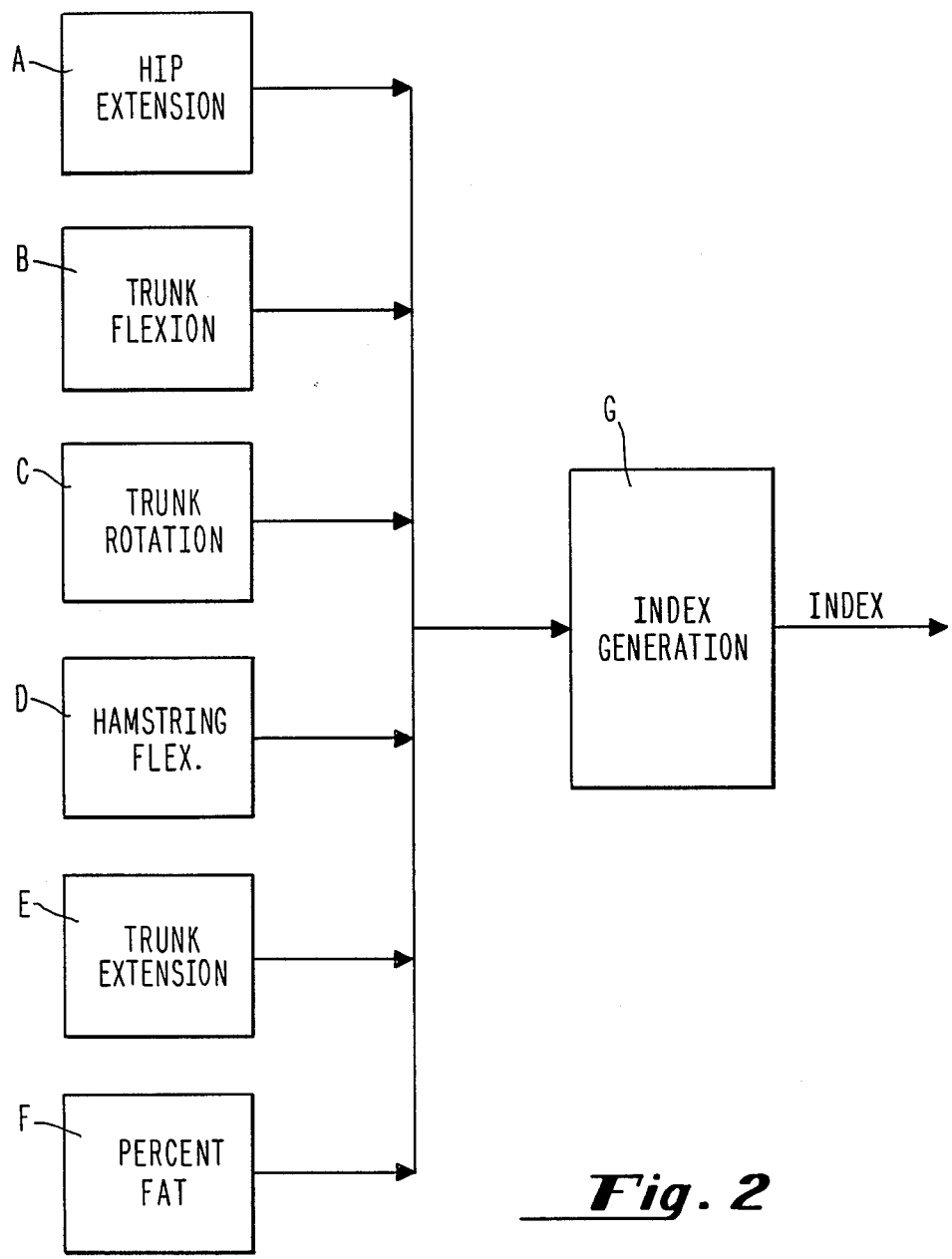
FIG. 2 is a schematic representation in block diagram form of one embodiment of the methods of the present invention.

By way of convenience and illustration but not by way of limitation, the methods according to the present invention can generally be divided into two aspects. With particular reference now to FIG. 2, the first aspect generally comprises the step of measuring the ability of a patient to perform certain movements with certain portions of the body, such as one or more of the measurements A through F indicated in FIG. 2. The second aspect relates to the generation of a numerical index based upon these measurements and an expected range of values thereof. The generation step is shown schematically in FIG. 2 as block G. The present invention thus provides methods for reliably producing a numerical index which is quantitatively indicative of the state of health of a patient's back. Moreover, since the method steps of the present invention are easily repeatable, the present methods may be beneficially used in a comprehensive program for the diagnosis and treatment of back injury. In this way, the treating physician or therapist will be able to accurately monitor the patient's back injury by conducting the method during successive visits by the patient. Such a comprehensive program is beneficial to the patient as well as the treating physician or therapist. That is, the physician or therapist will obtain the benefit of a quantitative diagnosis and the patient will be psychologically benefited by having an accurate and concrete representation of his or her progress towards recovery. For the purpose of convenience but not by way of limitation, the term physician is herein used to refer generally to the physician, therapist or any other person involved in conducting the methods of the present invention. Likewise, the term "patient" refers to all persons as may be evaluated by the methods and apparatus of the present invention, whether or not such persons are under the care of doctor.

According to the first aspect of the methods of the present invention, the ability of the patient to perform certain movements with certain parts of the body is measured. In particular, the ability of the patient to perform flexibility and strength movements is measured. These measurements generally comprise measuring the movements of a first portion of the patient's body while the patient attempts to maintain the remainder of the body in a substantially stationary position. However, as will be described in more detail below, the measurement may also comprise measuring the movement of the remaining portion when the first portion has been moved. The measurements will generally include angular measurements and/or measurements of linear distance.

Applicant has found that certain movements and certain measurement techniques are very important in quantifying the health or injury of a human back. More particularly, applicant has found that it is preferable for one or more of the following movements and the accompanying measurements to be utilized according to the methods of the present invention.

Hip Extension

Applicant has found that an important indicator in quantifying the extent of a back injury is the ability of a patient to perform certain hip extension movements, and that it is also important to quantify this ability using the measuring techniques of the present invention. More particularly, it is preferred that the patient is positioned on a rigid surface in a supine position with both knees drawn towards the chest as far as possible. According to a preferred practice of the present invention, the patient places the left hand on the left knee and the right hand on the right knee uses the support provided thereby to augment the lifting action towards the chest. Once in this initial position, the patient is instructed by the attending physician to release the right knee and slowly extend the right leg parallel to the rigid surface as far as possible. An important feature of certain aspects of the present invention resides in measuring the flexibility of a patient's back in performing this movement by measuring the angle subtended by the right femur. That is, the ability of a patient to move his or her right leg into a substantially extended position while holding his or her left leg towards the chest is an indication of the extent of back injury, and measuring of the angle subtended is a quantification of this indicator. While many means are available and well known in the art for performing such measurements, a goniometer, either manual or electrical, is preferred for this purpose. In particular, this measurement can be conducted by placing the stationary arm of the goniometer parallel to the flat surface upon which the patient is lying, with the axis of the goniometer at the right hip joint and the free arm of the goniometer along the patients right femur.

Repetition of the above described movements and measurements using the other side of the patients body is also an indication of the relative health of the patient's back and will provide a quantitative measure thereof. According to preferred practice, for example, the patient starts in the same initial position as described above, except in this movement the left leg is slowly extended while the right leg is maintained as close as possible to the chest. The angle subtended by the left femur is then measured by placing the stationary arm of the goniometer parallel to the flat surface upon which the patient is lying, with the axis of the goniometer at the left hip joint and the free arm of the goniometer on the patient's left femur.

Trunk Flexion

The applicant has found that another important indicator in quantifying the extent of a back injury is the ability of a patient to perform certain trunk flexion movements, and that it is also important to quantify this ability using the measuring techniques of the present invention. More particularly, movements according to this aspect of the present invention comprise initially positioning the patient in a supine position, preferably on a hard flat surface, with knees bent and feet flat on the surface. The heels of the feet are preferably approximately a distance of about one foot from the buttocks. In some embodiments, it may be desirable to additionally require the patient to place his or her arms across his or her chest with hands resting on opposite shoulders. Applicant has found that the ability of the patient to move from this initial position to a second position by slowly lifting and holding his or her head and shoulder blades off the table as high as possible also provides a good indication of back injury. According to some embodiments, it is preferable for the patient to maintain the soles of the feet firmly on the flat surface during this motion. The indication provided by this movement is preferably quantified by measuring the angle through which the patient's mid axilla passes as the patient moves from the initial to the second position. As the term is used herein, "midaxilla" refers to the portion of trunk of the patient which lies along the axis extending from about the hip joint to about the armpit. In particular, the stationary arm of the goniometer is placed parallel to the flat surface upon which the patient is lying, the axis of the goniometer at the hip joint. The free arm of the goniometer is placed along the patient's trunk pointing along the mid axilla. In general, a relatively large angular movement of the axilla is indicative of a relatively healthy back.

Trunk Rotation

The applicant has found that another important indicator in quantifying the extent of back injury is the ability of a patient to perform certain trunk rotation movements, and that it is also important to quantify this ability using the measuring technique of the present invention. More particularly, the initial position for this movement comprises the patient lying supine, preferably on a hard rigid surface, with knees bent and feet flat on the surface with heels a distance of about one foot from the buttocks. According to some embodiments of the present invention, it may be preferred for the initial position to also include the patient having the arms lying on the surface at his or her sides. From this initial position, the patient crosses the right leg over the left leg and then, without moving the left foot, slowly moves both legs as far as possible towards the hard rigid surface and to the right of the patient. An important feature of certain aspects of the present invention resides in measuring the flexibility of a patient's back in performing this movement by measuring the angle subtended by the left femur. That is, the ability of the patient to perform this movement is an indication of the relative health of the patient's back and the number of degrees through which the left femur of the patient travels during this motion is a quantification of this indicator. Once again, it may be preferred that a goniometer, either mechanical or electronic, be used to take such measurement. In particular, the stationary arm of the goniometer is placed perpendicular to the flat surface upon which the patient is lying, with the axis of the goniometer at the left hip joint of the patient. The free arm of the goniometer is placed along the patient's left femur and measures the arc through which the left femur moves.

Repetition of the above movements and measurements using the other side of the patient's body is also an indication of the relative health of the patient's back and the methods of the present invention will, likewise, provide a quantitative measure thereof. In particular, the patient starts in the same initial position as described above, except in this movement the left leg is crossed over the right and both legs are slowly moved as far as possible towards the rigid flat surface to the left side of the patient. The measurement of this movement is preferably taken by placing the stationary arm of the goniometer perpendicular to the table, with the axis of the goniometer at the right hip joint. The free arm of the goniometer is placed along the patient's right femur and measures the arc through which the right femur passes.

Hamstring Flexibility

Applicant has found that the hamstring flexibility of a patient is also generally a good indicator of the relative health of a patient's back. In a preferred embodiment, hamstring flexibility can be measured by positioning the patient in a sitting position with legs extended straight forward from the body. Bending at the hip, the patient fully stretches and holds the arms extended as far as possible forward of the body. In certain embodiments of the present invention, it is preferred that the patient extend his arms towards the toes of the feet and attempts to reach beyond the toes of the feet as far as possible while maintaining the remainder of the body in a stationary position. In particular, it is preferred for the patient to keep the legs straight and extended. The angle or linear distance through which the moving portions of the body travel provides an indication of the relative health of the patient's back. According to one preferred embodiment, this indication can be quantified by measuring the distance between the finger tips and the toes of the patient when the patient has reached his or her maximum extension.

Trunk Extension

Applicant has found that another important indicator in quantifying the extent of back injury is the ability of a patient to perform certain trunk extension movements, and that it is also important to quantify this ability using the measuring techniques of the present invention. More particularly, the initial position for this movement comprises the patient lying prone, preferably on a hard flat surface. According to some embodiments of the present invention, it is also preferred for the patient to interlock his hands behind his head in said prone position The movement then comprises requiring the patient to slowly lift and hold his elbows and chin as high as possible off the hard flat surface. The ability of the patient to carry out this movement is an indication of the relative health of the patient's back, and this indication is preferably quantified by measuring the linear distance between the bottom of the chin and the table.

Percent Fat

In addition to the movements and measurements described above, applicant has found that the health of a patient's back is also functionally related to the percentage of body fat carried by that person. In particular, applicant has found that including the measurement of body fat in the methods of the present invention aids in the quantification of back health. Although several techniques are well known in the art for determining the percent of body fat, it is preferred that such determination be made according to the methods described more fully hereinafter.

Using the above description as a basis and a guide, those skilled in the art will appreciate that other movements and measurements indicative of the health of a patient's back may also be conducted according to the methods of the present invention. These additional movements, whether used independently or in combination with one or more of the movements and measurements described above, are within the scope of the present invention.

As indicated briefly above, a second important aspect of the present invention resides in generating a quantitative index of back health based upon the movements and measurements conducted according to the first aspect of the present invention. In general, generating such an index comprises comparing at least one of the measurements as described above to an expected range of measurements, said range being representative of the range spanned between measurements of a healthy back and an injured back. For example, if for a given movement a certain body portion would be expected to move through a 60° angle if the back of the patient was perfectly healthy and a movement of 0° for that same movement would be indicative of an injured back, then the ability of a patient to move 55° with that same portion of the body provides a quantitative index of the extent of injury or health of the patient's back. For the purposes of simplicity and familarity, some preferred embodiments of the present invention present such an index on a percentage scale. That is, the index is obtained by first subtracting the minimum expected measurement from the working measurement, dividing by the expected range and then multiplying that ratio by 100 to produce the quantitative index of back injury. Obviously, an index of 100 represents a healthy back while an index of 0 represents an injured back. As the term is used herein, "working measurement" will generally refer to the measurement actually recorded by the physician or therapist. The "working measurement", however, also refers to actual measurements which have been adjusted to fall within the expected range, as more fully described hereinafter.

With particular regard to the preferred hip extension movement and measurement described above, a high value for the angle subtended by the femur is indicative of a relatively healthy back while a low value for the angle subtended is indicative of a relatively injured back. More particularly, applicant has found that movement resulting in a measurement of 170° or greater is representative of a relatively healthy back while a measurement of 135° or less is indicative of a relatively injured back. Using the percentage scale described above, therefore, the index should have a value of 100 when 170° or more is measured and a value of 0 when 135° or less is measured. In order to generate such an index, it is preferred that a working measurement be produced by adjusting the actual measurement to fall within the expected range. This is preferably achieved by increasing to the minimum expected value, i.e. 135°, any actual measurements which lie below the minimum expected value and by decreasing to the maximum expected value, i.e. 180°, any measurement which lies above the expected maximum value. The minimum expected value of 135° is then subtracted from the working measurement and this sum is then divided by the expected range, i.e. 45°. The quotient is multiplied by 100 to obtain the index for that movement. Unless otherwise indicated, this general technique of producing an index based upon the actual and working measurements is preferably utilized for each of the movements and measurements described herein.

With particular regard to the trunk flexion movement and measurement described above, a low value for the angle subtended by the axilla is indicative of a relatively injured back while a high value for the angle subtended is indicative of a relatively healthy back. More particularly, the applicant has found that movement resulting is a measurement of 45° or more is representative of a relatively healthy back while a measurement of 5° or less is indicative of a relatively injured back. Based upon an index using the percentage scale described above, therefore, the index should have a value of 0 when 5° or less is measured and a value of 100 when 45° or more of movement is measured.

With particular regard to the trunk rotation movement and measurement described above, a high value for the angle subtended by the femur is indicative of a normal healthy back while a low value of the angle subtended is indicative of a relatively injured back. More particularly, applicant has found that movement resulting in a measurement of 100° or more is representative of a relatively healthy back while a measurement of 50° or less is indicative of a relatively injured back. Using the percentage scale described above, therefore, the index should have a value of 0 when 50° or less is measured and a value of 100 when 100 or more is measured.

With particular regard to the hamstring flexibility movement and measurement described above, it is preferred that the measuring step comprise measuring the horizontal distance between the fingertips and a point along the legs of the patient. In particular, it is preferred that such a point is the point along the legs of the patient lying about 10 inches in front of (i.e.: on the knee side of) the toes. Based upon this measurement technique, applicant has found that a movement resulting in a measurement of 18 inches or more (i.e.: 8 or more inches past the tip of the toes) is representative of a normal healthy back, while a measurement of about 2 inches or less (i.e.: 8 inches or more in front of the toes) is indicative of a severely injured back. Using the percentage scale described above, therefore, the index should have a value of 0 when the measurement is equal to or less than about 2 inches and a value of 100 when the measurement is greater than or equal to about 18 inches.

With particular regard to the trunk extension movement and measurement described above, a high value for the distance between the chin and the surface upon which the patient is lying is indicative of a relatively healthy back while a low value is indicative of a relatively injured back. More particularly, applicant has found that a movement resulting in measurement of 12 inches or greater is representative of a normal healthy back while 2 inches or less is representative of a relatively injured back.

With regard to the measurement of body fat in male patients, the percent body fat may be determined by measuring skin fold sites at the following four locations: triceps, subscapular, suprailiac, and abdominal. Each of these measurements will generally be conducted with the patient standing erect with arms resting at the sides. At the tricep location, the physician will lift the skin fold midway between the acromion process and the olecranon process, aligned parallel to the humerus. Using skin fold calipers, the skin fold thickness is measured. In the subscapular region, the physician lifts the skin fold one inch below the inferior angle of the scapular, aligned diagonally with the opposite shoulder. Once again, the thickness of the skin fold is measured. At the suprailiac region, the physician lifts the skin fold one inch above the anterior superior iliac spine, aligned diagonally with the opposite hip. Once again, the thickness of the skin fold is measured. In the abdominal region, the physician lifts the skin fold one inch to the side of the umbilicus, aligned parallel to the spine. Once again the skin fold thickness is measured. The cumulative thickness of the skin folds at each of four sites is indicative of the percent of body fat of the patient being measured, as is well known in the art. For example, a cumulative thickness of 28 millimeters corresponds to approximately 10% body fat while a cumulative thickness of 113 millimeters corresponds to approximately 23% body fat. Applicant has found that for male patients, a measurement of 10% or less body fat is indicative of a healthy back while a measurement of 23% or more is indicative of an injured back. With respect to the percentage scale described above, an index of zero will correspond to a measurement of 23% or more while an index of 100 will correspond to 10% or less.

With regard to body fat measurements in female patients, the skin fold measurements are preferably taken at the following three locations: triceps, suprailiac, and quadriceps. The tricep and suprailiac measurements are taken as described above. At the quadricep location, the physician lifts the skin fold midway between the hip and the patella, aligned parallel to the femur. The thickness of the skin fold at this location is then measured. Once again, the cumulative thickness of the skin folds at the three locations is indicative of the percent body fat of the person being tested, as is well known in the art. For example, a cumulative thickness of 32 millimeters corresponds to approximately 14% body fat while a cumulative thickness of 71 millimeters corresponds to approximately 28% body fat. Applicant has found that for female patients, a measurement of 14% or less body fat is indicative of a healthy back while a measurement of 28% body fat or more is indicative of an injured back. With regard to the percentage scale described above, an index of zero will correspond to a measurement of 28% or more body fat while an index of 100 will correspond to a measurement of 14% or less body fat.

According to a preferred practice of the present invention, each measurements described above is combined to generate an overall quantitative index indicative of the relative health of the patient's back. It will be appreciated by those skilled in the art that it may be preferable to emphasis or "weigh" certain of these measurements more than others in determining an overall index for relative back health. That is, the treating physician may determine that certain of the measurements are more important or are better indicators of relative back health than others. Accordingly, methods of the present invention provide the step of weighing the various measurements such that the combination of the measurements is the most accurate representation of relative health of the patient's back. Accordingly, it is preferred that each of the movements and measurements described above is performed and that the measurements so obtained are combined as described herein to generate an overall index. More particularly, applicant has found that it is preferable to weigh each of the eight measurements described above according to the table given below:

| Measurement | Relative Weight in Overall Index |
|---|---|
| Right hip extension | 7.5 |
| Left hip extension | 7.5 |
| Trunk flexion | 15 |
| Right trunk rotation | 7.5 |
| Left trunk rotation | 7.5 |
| Hamstring flexibility | 20 |
| Trunk extension | 20 |
| Percent Flat | 15 |
| | 100 |

Accordingly, when each of the above described movements and measurements is utilized according to the methods of the present invention, it is preferred that an overall index be calculated according to the formula given below:

$$\begin{aligned}\text{Overall Index} &= \frac{RHE - 135}{35} \times 7.5 \\ &+ \frac{LHE - 135}{35} \times 7.5 \\ &+ \frac{TF - 5}{40} \times 15 \\ &+ \frac{RTR - 50}{50} \times 7.5 \\ &+ \frac{LTR - 50}{50} \times 7.5 \\ &+ \frac{HF - 2}{16} \times 20 \\ &+ \frac{TE - 2}{10} \times 20 \\ &+ \frac{[1 - (PBF - MEBF)]}{BFR} \times 15\end{aligned}$$

where:
RHE is the working measurement of the right hip extension movement;
LHE is the working measurement of the left hip extension movement;
RTR is the working measurement of the right trunk rotation movement;
LTR is the working measurement of the left trunk rotation movement;
TF is the working measurement of the trunk flexion movement;
HF is the working measurement of the hamstring flexibility movement;
TE is the working measurement of the trunk extension movement;
PBF is the working measurement of body fat;
MEBF is the minimum expected body fat (eg: 14% for females and 10% for males); and
BFR is the expected body fat range (eg: 14% for females and 13% for males).

EXAMPLE

The methods of the present invention are carried out on a male patient following actual measurements taken:

| Trunk Flexion | 50° |
|---|---|
| Left Trunk Rotation | 80° |
| Right Trunk Rotation | 75° |
| Hamstring Flexibility | 0 inches |
| Trunk Extension | 10 inches |
| Percent Body Fat | 15% |

Since the measurements for hip extension, trunk rotation, trunk extension, and body fat are within the expected ranges, the working measurements for these indicia are equivalent to the actual measurements. However, the actual measurement of 50° for the trunk flexion is above the maximum expected measurement of 45°. Accordingly, the working measurement for this movement is 45°. The measurement of zero inches for the hamstring flexion, on the other hand, is below the minimum expected value of 2 inches expected for this movement. Accordingly, the working measurement for this movement is 2 inches.

Based upon the working measurements described above and the formula disclosed herein, the overall index for this patient is calculated to be 58.34.

According to a preferred embodiment of the present invention, the method steps described above for achieving either an overall or an individual index may be repeated on successive occasions to aid in a comprehensive program for back injury treatment and rehabilitation. More particularly, it is anticipated that use of the overall index as described above will allow physicians to initially assess the extent of back injury of a particular patient and to track the progress towards recovery by periodically repeating the method. In this way, the methods of the present invention provide not only a diagnostic tool for the treating physician but also a therapeutic tool insofar as it will encourage the patient to continually increase the overall index. As result, it is preferred that the methods of the present invention be incorporated in a comprehensive program for the treatment and care of back injury.

Figure 1:
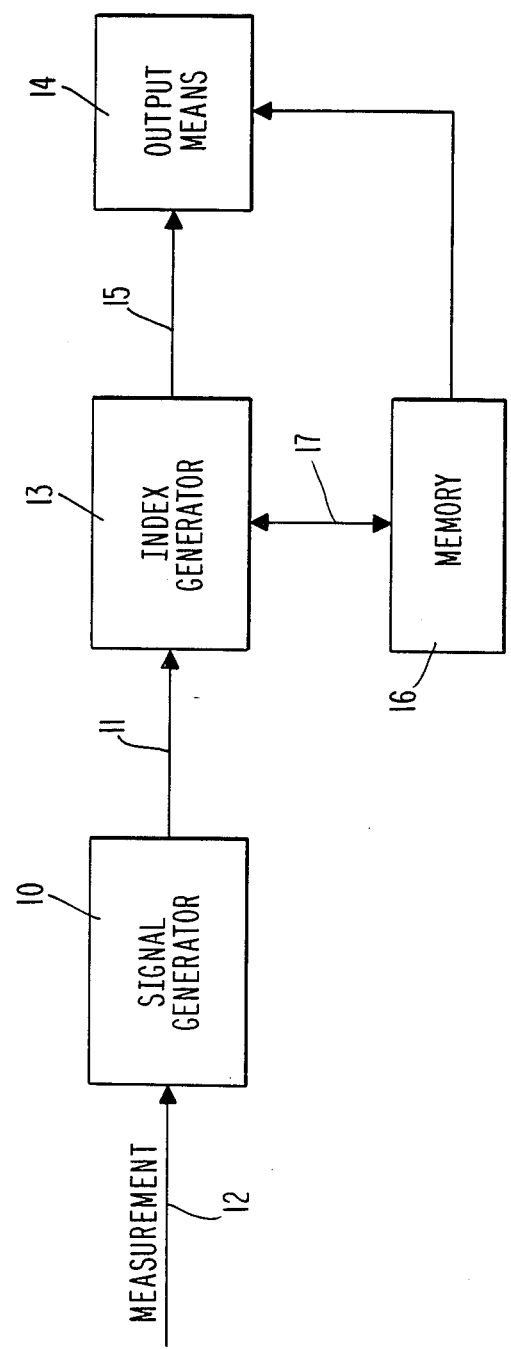
FIG. 1 is a schematic representation in block diagram form of an apparatus according to one embodiment of the apparatus of the present invention.

Applicant has found that the methods steps of the present invention, particularly those steps relating directly to the generation of an individual or overall index, may be carried out on an apparatus which includes or is coupled to a computer, microprocessor, or other electronic circuit means. For example, a computer can be used to provide means for generating an overall numerical index based upon the measurements described above. While it is clear that such measurements may be manually entered into the computer, it is preferred according to some embodiments of the present invention to provide a means for automatically and/or electronically providing said measured values to the generating means. Referring now to FIG. 1, a signal generator 10 is provided which generates a signal 11 based upon one or more of the measurements 12 described above. While signal generator 10 can be any apparatus known in the art capable of performing the function described, it is preferred according to certain embodiments of the present invention that an electronic goniometer of the type disclosed in U.S. Pat. No. 4,306,571 to McLeod, Jr., which is incorporated herein by reference, comprise the signal generator of the present invention. It will be appreciated by those skilled in the art that the signal generator disclosed therein may be readily adapted to perform the measurements described above. The signal generator 10 is coupled to index generator 13 and receives signals 11 therefrom. The index generator, which may be a computer or microprocessor, provides a means for generating either an individual index or an overall index value. The index generator 13 then provides signals 15 representative of the generated index to output means 14. As is well known in the art, output means 14 may be an LED display, a liquid crystal display, a hard copy printer, or any other means well known in the art for outputting the index thus generated. It may also be preferable according to certain embodiments of the present invention to provide an external memory 16 coupled, as at 17, with index generator 13. In this way, information relating to previously generated overall indices may be output along with the index generated during any current visit.

It will be appreciated by those skilled in the art that the form of the invention shown and described above is presented by way of illustration only. Various other changes may be made in the particular form and details of the invention without departing from the scope of the invention as defined in the claims which follow.

What is claimed is:

1. A method of establishing a quantitative index representative of the extent of back injury in a human patient comprising:
   (a) positioning the patient in a first position, said first position including said patient lying supine on a rigid surface with both legs held as close as possible to the chest;
   (b) measuring the angle through which the right femur of the patient passes as the patient slowly moves from said first position to a second position, said second position including the right leg of said patient being extended by said patient as far as possible along said rigid surface while said patient attempts to maintain the remainder of the body substantially as in said first position;
   (c) measuring the angle through which the left femur of the patient passes as the patient slowly moves from said first position to a third position, said third position including the left leg of said patient being extended by said patient as far as possible along said rigid surface while said patient attempts to maintain the remainder of the body substantially as in said first position;
   (d) positioning the patient in a fourth position on a rigid surface, said fourth position including said patient lying supine with knees bent and the heels at a distance of about 1 foot from the buttocks;
   (e) measuring the angle through which the mid axilla passes as the patient moves from said fourth position to a fifth position, said fifth position including said patient holding the head and shoulder blades as high as possible off the rigid surface while maintaining the remainder of the body substantially in said fourth position;
   (f) measuring the angle through which the left femur passes as the patient moves from said fourth position to a sixth position, said sixth position including the right leg being crossed over the left leg and the left knee being held by the patient as close as possible to the rigid surface and to the right of the patient;
   (g) measuring the angle through which the right femur passes as the patient moves from said fourth position to a seventh position, said seventh position including the left leg being crossed over the right leg and the right knee of the patient being held as close as possible to the rigid surface and to the left of the patient;
   (h) positioning the patient in an eighth position, said eighth position including said patient sitting with legs extended and together, the soles of the feet being substantially vertical;
   (i) measuring the horizontal distance between the fingertips of the patient and the point along the legs about eight inches in front of the toes of the patient after the patient moves from the eighth position to a ninth position, the ninth position including the patient being bent at the waist as far forward as possible and with arms at maximum extension;
   (j) positioning the patient in a tenth position, said tenth position including said patient lying prone on a rigid surface with chin lifted by the patient as far as possible off the rigid surface;
   (k) measuring the vertical distance between the bottom of the chin and the rigid surface with the patient in said tenth position;
   (l) providing an expected range of values for each of said measurements; and
   (m) comparing each of said actual measurements to said expected range to generate an overall index value representative of the extent of back injury of the patient.

2. The method of claim 1 wherein said expected range of values for the measurements of steps (b) and (c), is from about 135° to about 170°.

3. The method of claim 2 wherein said expected range of values, for the measurement of step (e) is from about 5° to about 45°.

4. The method of claim 3 wherein said expected range of values for the measurements of steps (f) and (g) is from about 50° to about 100°.

5. The method of claim 4 wherein said expected range of values for the measurement of step (i) is from about 2 inches to about 18 inches.

6. The method of claim 5 wherein said expected range of values for the measurement of step (k) is from about 2 inches to about 12 inches.

7. The method of claim 6 further comprising measuring the percent of body fat of the patient and wherein the expected range of values for the body fat measurement is from about 10% to about 23% for male patients and from about 14% to about 28% for female patients.

8. The method of claim 7 wherein said overall index value comprises a combination of individual index values, said individual index values comprising each of said measurements being converted to a working measurement and then divided by its respective expected range of measurements.

9. The method of claim 8 wherein said combination of individual index values comprises a weighted combination of said individual index values.

10. The method of claim 1 further comprising measuring the percent of body fat of the patient.

11. The method of claim 7 wherein the expected range of values for the body fat measurement is from about 0% to about 23% for male patients and from about 14% to about 28% for female patients.

12. A method of quantitatively determining the extent of back injury of a human patient comprising:
   (a) positioning the patient in a first position, said first position including said patient lying supine on a rigid surface with both legs held as close as possible to the chest;
   (b) measuring the ability of the patient to perform a movement with a first portion of the body while attempting to maintain the remainder of the body in a substantially stationary position, said movement being indicative of the relative health of the patient's back, said measuring step including the step of measuring the angle through which the femur of a first leg of the patient passes as the patient moves from said first position to a second position, said second position including the first leg of the patient being extended by said patient as far as possible along said rigid surface while said patient attempts to maintain the second leg substantially as in said first position; and (c) generating an index indicative of the relative health of the patient's back, including comparing said measured value to an expected range of measured values.

13. The method of claim 12 wherein the expected range of values for the measurement is from about 135° to about 170°, and wherein a measurement of about 170° or more is indicative of a healthy back and a measurement of about 135° or less is indicative of an injured back.

14. The method of claim 13 wherein said generating step comprises establishing the ratio between said measured value and said expected range of measured values.

15. The method of claim 12 wherein said first positioning includes said patient lying supine on a rigid surface with knees bent and the heels a distance of about one foot from the buttocks, and wherein said measuring includes measuring the angle through which the patients mid axilla passes as the patient moves from said first position to a second position, said second position including said patient holding the head and shoulder blades as high as possible off the rigid surface while maintaining the remainder of the body substantially as in said first position.

16. The method of claim 15 wherein said expected range of values for said measurement is from about 5° to about 45°, and wherein a measurement of about 45° or more is indicative of a healthy back and a measurement of about 5° or less is indicative of an injured back.

17. The method of claim 16 wherein said generating step comprises establishing the ratio between said measured value and said expected range of measured values.

18. The method of claim 12 wherein said first position comprises said patient lying supine with knees bent and the heels a distance of about one foot from the buttocks, and wherein said measuring step comprises measuring the angle through which the femur of a first leg of the patient passes as the patient moves from said first position to a second position, said second position including the second leg being crossed over the first leg and the knee of said first leg of the patient being as low as possible on the second leg side of the patient.

19. The apparatus of claim 18 wherein said expected range of values for said measurement is from about 50° to about 100°, and wherein measurement of about 50° or less is indicative of an injured back and a measurement of about 100° or more is indicative of a healthy back.

20. The method of claim 19 wherein said generating step comprises establishing the ratio between said measured value and said expected range of measured values.

21. The method of claim 12 wherein said first position comprises said patient sitting with legs extended together, the soles of the feet being substantially vertical, and wherein the measuring step comprises measuring the horizontal distance between the fingertips of the patient and the point along the legs about eight inches in front of the toes of the patient after the patient moves from said first position to a second position, the second position including the patient being bent at the waist as far forward as possible and with arms extended as far as possible.

22. The method of claim 12 wherein said first position comprises said patient lying prone on a rigid surface with the chin lifted as far as possible off the rigid surface and wherein said measuring step comprises measuring the vertical distance between the bottom of the chin and the rigid surface.

23. A method of quantitatively determining the extent of back injury of a human patient comprising:
(a) positioning the patient in a first position;
(b) measuring the ability of the patient to perform movement with the first portion of the body while attempting to maintain the remainder of the body in a substantially stationary position, said movement being indicative of the relative health of the patient's back, said measuring step including the step of measuring the extent of motion of said first portion, said remaining portion, or both;
(c) measuring the percentage of body fat of the patient; and
(d) generating an index indicative of the relative health of the patient's back including comparing said measured values to an expected range of measured values.

24. The method of claim 23 wherein said generating step comprises establishing a ratio between each of said measured values and the respective expected range of said measured value.

25. The method of claim 24 wherein the patient is a male patient and the expected range of values for said body fat measurement is from about 10% to about 23%, and wherein a measurement of about 10% or less is indicative of a healthy back and a measurement of about 23% or more is indicative of an injured back.

26. The method of claim 24 wherein said expected range of values for said percent body fat is from about 14% to about 28%, and wherein a measurement of about 14% or less is indicative of a healthy back and a measurement of 28% or more is indicative of an injured back.

* * * * *